United States Patent

Köhn et al.

Patent Number: 5,248,810
Date of Patent: Sep. 28, 1993

[54] HALOGENATED OLEFINS, PROCESSES FOR THEIR PREPARATION AND THEIR USE AS PESTICIDES

[75] Inventors: Arnim Köhn; Günter Hömberger; Hartmut Joppien; Harald von Keyserlingk, all of Berlin, Fed. Rep. of Germany

[73] Assignee: Schering Aktiengesellschaft, Fed. Rep. of Germany

[21] Appl. No.: 626,991

[22] Filed: Dec. 13, 1990

[30] Foreign Application Priority Data

Dec. 15, 1989 [DE] Fed. Rep. of Germany ....... 3941966

[51] Int. Cl.$^5$ ..................... C07C 69/65; A01N 37/06
[52] U.S. Cl. ..................... 560/219; 560/221
[58] Field of Search ............... 560/219, 221; 514/549

[56] References Cited

U.S. PATENT DOCUMENTS 4,161,536  7/1979  Drabek et al. ............... 560/219
4,409,238 10/1983  Mori et al. ............... 560/219
4,950,666  8/1990  Peake et al. ............... 514/227.5

Primary Examiner—José G. Dees
Assistant Examiner—B. Frazier
Attorney, Agent, or Firm—Ostrolenk, Faber, Gerb & Soffen

[57] ABSTRACT

This are described new halogenated olefines of general formula I

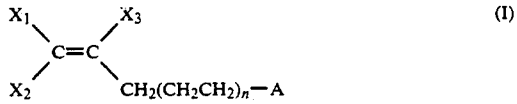

in which $X_1$, $X_2$, $X_3$, n and A have the meanings given in the description as well as processes for their preparation. The compounds can be used as pesticides especially against insects and acarids.

3 Claims, No Drawings

HALOGENATED OLEFINS, PROCESSES FOR THEIR PREPARATION AND THEIR USE AS PESTICIDES

This invention relates to new halogenated olefines, processes for their preparation and their use as pesticides especially against insects and mites.

Certain substituted alkenes (EP 227 369) and dihaloalkenes (EP 247 484) with insecticidal activity are known.

It has now been found that halogenated olefines of general formula I

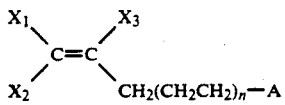

in which
$X_1$ is fluorine or chlorine;
$X_2$ is fluorine;
$X_3$ is hydrogen, methyl, ethyl, halomethyl, phenyl, fluorine, chlorine or bromine;
n is 0, 1, 2 or 3 and
A is

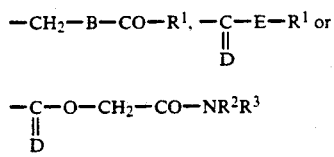

in which
B is oxygen or sulphur,
D is oxygen, sulphur or two hydrogen atoms,
E is oxygen, sulphur or $NR^4$,
$R^1$ is hydrogen, an alkali metal atoms, an equivalent of a divalent atom or an ammonium or phosphonium cation with 0-4 alkyl, aryl or aralkyl groups, $C_{1-20}$-alkyl, $C_{2-20}$-alkenyl, $C_{2-20}$-alkynyl, halo-$C_{1-10}$-alkyl, halo-$C_{2-10}$-alkenyl, $C_{2-6}$-alkenylphenyl, $C_{1-6}$-alkylphenyl-$C_{1-6}$-alkoxy, $C_{2-6}$-alkynyloxyphenyl-$C_{2-6}$-alkenyl, $C_{1-6}$-alkoxyphenyl-$C_{2-6}$-alkenyl, hydroxyphenyl-$C_{2-6}$-alkenyl, $C_{3-6}$-cycloalkyl, $C_{1-3}$-alkyl-$C_{3-6}$-cycloalkyl, $C_{3-6}$-cycloalkyl-$C_{1-6}$-alkyl, halo-$C_{3-6}$-cycloalkyl-$C_{1-6}$-alkyl, bicycloalkyl, chlorofluorocyclopropylethylcarbonyloxy-$C_{1-10}$-alkyl, chlorofluorocyclopropylcarbonyloxy-$C_{1-3}$-alkoxy-chlorofluorocyclopropylcarbonyl-$C_{1-3}$-alkoxy-$C_{1-3}$-alkyl, aryl-$C_{1-6}$-alkyl, aryl-$C_{2-6}$-alkenyl, halo-aryl-$C_{1-6}$-alkyl, $C_{1-4}$-alkylaryl-$C_{1-4}$-alkyl, haloaryl-$C_{2-6}$-alkenyl, halo-$C_{1-4}$-alkylaryl-$C_{1-6}$-alkyl, $C_{1-3}$-alkoxyaryl-$C_{1-6}$-alkyl, aryloxybenzyl, α-$C_{1-3}$-alkylphenoxybenzyl, halophenyl(cyclopropyl)-$C_{1-3}$-alkyl, halophenoxy-$C_{1-6}$-alkyl, naphthyl-$C_{1-6}$-alkyl, chloro, tetrahydropyranyl, aryl, optionally substituted, one or more times, by $C_{1-20}$-alkyl, halo-$C_{1-6}$alkyl, $C_{1-16}$-alkoxy, halo-$C_{1-6}$-alkoxy, phenyl-$C_{1-6}$-alkyl, phenyl-$C_{1-6}$-alkoxy-$C_{3-10}$-cycloalkoxy, halo-$C_{3-10}$-cycloalkoxy, $C_{3-6}$-cycloalkenyloxy, halo-$C_{3-6}$-cycloalkenyloxy, $C_{2-6}$alkenyloxy, halo-$C_{2-6}$-alkenyloxy, $C_{2-6}$-alkynyloxy, halo-$C_{2-6}$-alkynyloxy, alkylsulphonyloxy, alkylphenylsulphonyloxy, haloalkylsulphonyloxy, phenyl, halo, amino, cyano, hydroxy, nitro, aryloxy, heteroaryloxy, haloaryloxy, arylamino, haloarylamino, $C_{1-6}$-alkoxycarbonyl, $C_{1-6}$-alkoxycarbonylmethyl, halo-$C_{1-6}$-alkoxycarbonyl, $C_{1-2}$-alkyldioxy, $C_{1-6}$-alkylthio, halo-$C_{3-6}$-cycloalkylalkylamino, halo-$C_{3-6}$-cycloalkylalkylcarbonyloxy, $C_{1-6}$-alkylamino or di-$C_{1-6}$-alkylamino, heteroaryl, optionally substituted by halogen, $C_{1-3}$-alkyl or halo-$C_{1-3}$-alkyl, $R^2$ and $R^3$, independently of each other, are hydrogen, $C_{1-20}$-alkyl, $C_{2-20}$-alkenyl, $C_{2-20}$-alkynyl, halo-$C_{1-10}$-alkyl, $C_{3-6}$-cycloalkyl, $C_{1-3}$-alkyl-$C_{3-6}$-cycloalkyl, $C_{3-6}$-cycloalkyl-$C_{1-6}$-alkyl, halo-$C_{3-6}$-cycloalkyl-$C_{1-6}$-alkyl, bicycloalkyl, aryl-$C_{1-6}$-alkyl, aryl-$C_{2-6}$-alkenyl, haloaryl-$C_{1-6}$-alkyl, $C_{1-4}$-alkylaryl-$C_{1-4}$-alkyl, haloaryl-$C_{2-6}$-alkenyl, halo-$C_{1-4}$-alkylaryl-$C_{1-6}$-alkyl, $C_{1-3}$alkoxyaryl-$C_{1-6}$-alkyl, aryloxybenzyl, halophenyl(cyclopropyl)-$C_{1-3}$-alkyl, halophenoxy-$C_{1-6}$-alkyl, naphthyl-$C_{1-6}$-alkyl, aryl, optionally substituted, one or more times, by $C_{1-20}$-alkyl, halo-$C_{1-6}$-alkyl, $C_{1-16}$-alkoxy, halo-$C_{1-6}$-alkoxy, phenyl-$C_{1-6}$-alkyl, phenyl-$C_{1-6}$-alkoxy, $C_{3-10}$-cycloalkoxy, halo-$C_{3-10}$-cycloalkoxy, $C_{3-6}$cycloalkylalkoxy, halo-$C_{3-6}$cycloalkylalkoxy, $C_{2-6}$-alkenyloxy, halo-$C_{2-6}$-alkenyloxy, $C_{2-6}$-alkynyloxy, alkylsulphonyloxy, haloalkylsulphonyloxy, phenyl, halo, amino, cyano, hydroxy, nitro, $C_{1-6}$-alkoxycarbonyl, $C_{1-6}$-alkoxycarbonylmethyl, halo-$C_{1-6}$-alkoxycarbonyl, $C_{1-2}$-alkyldioxy, $C_{1-6}$-alkylthio, halo-$C_{3-6}$-cycloalkylalkylcarbonyloxy, $C_{1-6}$-alkylamino or di-$C_{1-6}$-alkylamino, heteroaryl, optionally substituted by halogen, $C_{1-3}$-alkyl or halo-$C_{1-3}$-alkyl, or $R^2$ and $R^3$ together with the N-atom to which they are attached form a saturated or unsaturated heterocyclic ring, $R^4$ is hydrogen or —$CH(R^6)COOR^6$, $R^5$ is hydrogen, $C_{1-20}$-alkyl, $C_{2-20}$-alkenyl, $C_{2-20}$-alkynyl, optionally substituted benzyl, aryl or heteroaryl, as well as $C_{1-20}$-alkyl, $C_{2-20}$alkenyl and $C_{2-20}$-alkynyl, substituted by —Y—R;, —COOR;, —$NR^7R^8$, —O-CONH$_2$, —NH—C(=NH)—NH$_2$, $R^7$ and $R^8$ are hydrogen or $C_{1-6}$-alkyl, Y is oxygen or sulphur, and $R^6$ is hydrogen, an alkali metal atom, a corresponding equivalent of a divalent atom or an ammonium or phosphonium cation with 0-4 alkyl, aryl or aralkyl groups, $C_{1-20}$-alkyl, $C_{2-20}$-alkenyl, $C_{2-20}$-alkynyl, halo-$C_{3-6}$-cycloalkyl-$C_{1-6}$-alkyl, $C_{3-6}$-cycloalkyl, $C_{1-3}$alkyl-$C_{3-6}$-cycloalkyl, decalinyl, difluorocyclopropylethylcarbonyloxy-$C_{1-10}$-alkyl, difluorocyclopropylcarbonyloxydecalinyl, difluorocyclopropylethylcarbonyloxy-$C_{1-3}$-alkoxy-$C_{1-3}$-alkyl, phenyl-$C_{1-6}$-alkyl, phenyl-$C_{2-6}$-alkenyl, halobenzyl, $C_{1-4}$alkylbenzyl, $C_{1-3}$-alkoxyphenyl-$C_{1-6}$-alkyl, phenoxybenzyl, α-cyanophenoxybenzyl, α-$C_{1-3}$-alkylphenoxybenzyl, halophenoxy-$C_{1-6}$-alkyl, naphthyl-$C_{1-6}$-alkyl, aryl, optionally substituted, one or more times, by $C_{1-20}$-alkyl, halo-$C_{1-6}$-alkyl, $C_{1-16}$-alkoxy, halo-$C_{1-6}$-alkoxy, phenyl-$C_{1-6}$-alkyl, phenyl-$C_{1-6}$-alkoxy, $C_{3-10}$-cycloalkoxy, halo-$C_{3-10}$-cycloalkoxy, $C_{3-6}$-cycloalkylalkoxy, halo-$C_{3-6}$-cycloalkylalkoxy, $C_{2-6}$-alkenyloxy, halo-$C_{2-6}$-alkenyloxy, $C_{2-6}$-alkynyloxy, halo-$C_{2-6}$-alkynyloxy, alkylsulphonyloxy, alkylphenylsulphonyloxy, haloalkylsulphonyloxy, phenyl, halo, amino, cyano, hydroxy, nitro, aryloxy, heteroaryloxy, haloaryloxy, arylamino, haloarylamino, $C_{1-6}$-alkoxycarbonyl, $C_{1-6}$alkoxycarbonylmethyl, halo-$C_{1-6}$alkoxycarbonyl, $C_{1-2}$-alkyldioxy, $C_{1-6}$-alkylthio, halo-$C_{3-6}$-cycloalkylalkylamino, halo-$C_{3-6}$-cycloalkylalkylcarbonyloxy, $C_{1-6}$-alkylamino or di-$C_{1-6}$-alkylamino, heteroaryl, optionally substituted by halogen, $C_{1-3}$-alkyl or halo-$C_{1-3}$-alkyl, and $R^4$ and $R^1$ together with the N-atom to which they are attached can form a saturated or unsaturated heterocyclic ring, with the proviso that when $X_1$ and $X_3$ are both fluoro or when $X_1$ is chloro and $X_3$ is hydrogen, n is not 0, and when $X_1$ is fluoro and $X_3$ is trifluoromethyl and n is 0, $R^1$ is not ethyl, show better insecticidal and acaricidal activity in comparison to the known compounds of related structure.

Preferred compounds are those where $X_1$ is fluoro.

The term "alkyl" includes straight and branched carbon chains.

The term "alkenyl" includes straight and branched carbon chains that can contain one or more double bonds. The term "alkynyl" includes straight and branched carbon chains that can contain one or more triple bonds.

The term "aryl" means one to three ringed aromatic groups, such as phenyl, naphthyl or phenanthryl.

The term "heteroaryl" means a 5- or 6-membered ring that contains one or more nitrogen, oxygen or sulphur atoms that can be saturated or partially saturated and can optionally carry a fused benzo ring, eg pyridine, thiazole or chromene.

When $R^2$ and $R^3$ as well as $R^1$ and $R^4$ together with the atom to which they are attached form a saturated or unsaturated heterocyclic ring, these may be for example morpholino, piperidino, pyrrolo, imidazolo, triazolo or pyrrolidino.

The compounds of general formula I can exist as mixtures of optical isomers. In such cases the invention also includes the individual isomers of the compounds of formula I as well as their mixtures.

The invention also includes compounds of the general formula II

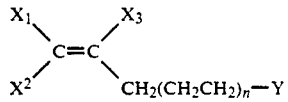

(II)

in which $X_1$, $X_2$, $X_3$ and n have the meanings given in formula I and Y is —COOH, —COCl, —COBr or —CN, with the proviso that when $X=Cl$ and $n=0$, Y is not —COOH.

Further, the invention includes to compounds of formula III

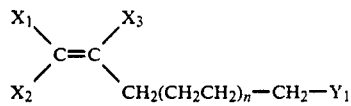

(III)

in which $X_1$, $X_2$, and $X_3$ and n have the meanings given in general formula I and Y, is OH, Cl or Br, with the proviso a) when $X_1$ and $X_3$ are both fluorine and n is 0, $Y_1$ is not OH or bromine, b) when $X_1$ is fluorine, $X_3$ is trifluoromethyl and n is 0, $Y_1$ is not OH, and c) when $X_1$ is chlorine and $Y_1$ is bromine, n is not 0.

The compounds of general formula II and III are intermediates in the preparation of the compounds of the invention of formula I. They are also insecticidally and acaricidally active in their own right. The compounds of the invention of general formula I in which A is —CO—E—$R^1$, can be prepared by a process in which a) an acid halide of general formula II

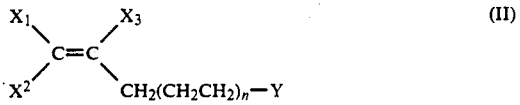

(II)

wherein $X_1$, $X_2$ and $X_3$ and n have the meanings given in general formula I and Y is COCl or COBr, is reacted with an alcohol or amine of formula IV $$H-E-R^1 \quad (IV)$$

wherein E and $R^1$ have the meanings give in general formula I, optionally in a solvent in the presence of an acid acceptor, or b) an acid of general formula II

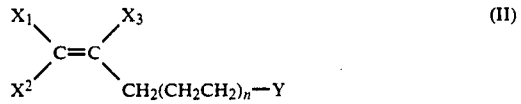

(II)

wherein $X_1$, $X_2$ and $X_3$ have the meanings given in general formula I and Y is COOH, is reacted with an alcohol or amine of general formula IV, optionally using a solvent in the presence of a catalyst, or c) an acid of general formula V $$X_3-CO-CH_2-(CH_2CH_2)_n-COOH \quad (V)$$

wherein $X_3$ and n have the meanings given in general formula I, is reacted with an alcohol or amine of formula IV, optionally in a solvent in the presence of a catalyst or a dehydrating agent, to given an intermediate compound of formula VI $$X_3-CO-CH_2-(CH_2CH_2)_n-CO-E-R^1 \quad (VI)$$

wherein $X_3$, n, E and $R^1$ have the meanings given in general formula I and, in the presence of an inert solvent, this is reacted with a halomethane or an alkaline metal salt of a trihaloacetic acid and a trisubstituted phosphine, or d) an alcohol of general formula III

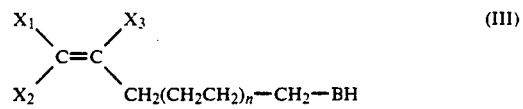

(III)

in which $X_1$, $X_2$, $X_3$, n and B have the meanings given in general formula I, is reacted with an oxidising agent, optionally using a solvent, to given an acid of general formula II which is then further treated according to process variant b), or e) a halide of general formula VII

(VII)

in which $X_1$, $X_2$, $X_3$ and n have the meanings given in general formula I and $Y_1$ is chlorine, bromine or iodine, is reacted, optionally in the presence of a solvent, with an anion of a diester or malonic acid of general formula VIII

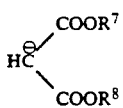
(VIII)

wherein $R^7$ and $R^8$, independently of each other are $C_{1-10}$-alkyl, aryl or benzyl, to given an intermediate compound of general formula IX

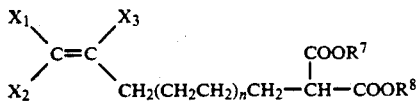
(IX)

wherein $X_1$, $X_2$, $X_3$ and n have the meanings given in general formula I and $R^7$ and $R^8$ have the meanings given above and this is then converted by acid or alkaline hydrolysis to give an intermediate compound of general formula X

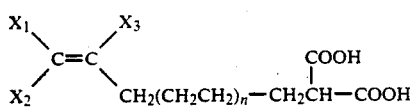
(IX)

in which $X_1$, $X_2$, $X_3$ and n have the meaning given in general formula I and this is monodecarboxylated by heating or by using a catalyst, optionally in the presence of the solvent, and then further reacted according to process variant a) or b), or f) a nitrile of general formula XI $$X_3-CO-CH_2-(CH_2CH_2)_n-CN \quad (XI)$$

in which $X_3$ and n have the meanings given in general formula I is reacted with an alkali metal salt of a trihaloacetic acid or a halomethane of general formula XX

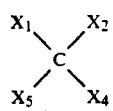
(XX)

in which $X_1$ and $X_2$ have the meanings given in general formula I, $X_4$ is halogen or hydrogen and $X_5$ is halogen, to give an intermediate product of general formula XII

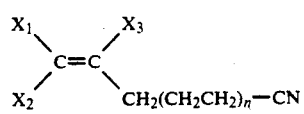
(XII)

in which $X_1$, $X_2$, $X_3$ and n have the meanings give in general formula I and this is then reacted with an alcohol or amine of general formula IV, optionally using a solvent, in the presence of an acid, or g) an ester of general formula XXI

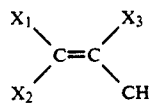
(XXI)

in which $X_1$, $X_2$, $X_3$, n, E and $R^1$ have the meanings given in general formula I, is reacted with an alcohol or an amine of general formula IV, optionally using a solvent, and using an acid or basic catalyst.

The compounds of the invention of general formula I in which A is

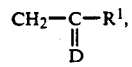

can be prepared by a process in which h) an alcohol of general formula III

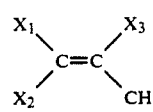
(III)

in which $X_1$, $X_2$, $X_3$ and n have the meanings given in general formula I is reacted with an acid of general formula XIII

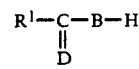
(XIII)

in which B, D and $R^1$ have the meaning given in general formula I, optionally using a solvent as well as a catalyst, or i) an alcohol of general formula III is reacted with an acid halide of general formula XIV $$R^1-CO-Y_1 \quad (XIV)$$

in which $Y_1$ is chlorine or bromine and $R^1$ has the meaning given in general formula I, optionally using a solvent as well as an acid acceptor, or j) an alcohol of general formula XV $$X_3-CO-CH_2-(CH_2CH_2)_n-CH_2OH \quad (XV)$$

wherein n and $X_3$ have the meanings given in general formula I, is reacted with an acid of general formula XIII, optionally using a solvent as well as a catalyst, to give an intermediate compound of general formula XVI

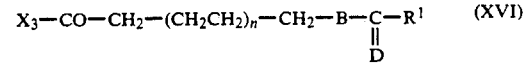
(XVI)

in which $X_3$, n, B, D and $R^1$ have the meanings given in general formula I and then, in the presence of an inert solvent, this is reacted with a halogenated $C_1$-unit according to process variant c), or k) an alcohol of general formula XV is reacted with an acid halide of general formula XIV, optionally using a solvent as well as an acid acceptor, to give an intermediate compound of general formula XVI and this is then reacted with a halogenated $C_1$-unit according to process variant c), or l) a halide of general formula XVII

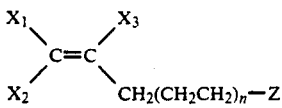

in which $X_1$, $X_2$, $X_3$ and n have the meanings given in general formula I and Z is chlorine, bromine or iodine, is reacted with a carboxylate salt of general formula XVIII $$R^1COOM \qquad (XVIII)$$

in which $R^1$ has the meaning given in general formula I and M is a monovalent metal or the corresponding equivalent of a multivalent metal, optionally using a solvent as well as a catalyst, or m) an acid or ester of general formula XIX

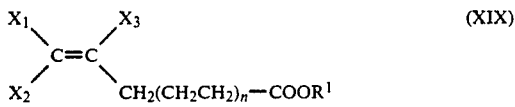

in which $X_1$, $X_2$, $X_3$, n and $R^1$ have the meanings given in general formula I is reacted with a reducing agent, optionally using a solvent, to give an alcohol of general formula III which is then treated according to process variant d) or e).

The reactions can be carried out over a wide temperature range. Generally they are carried out at a temperature between $-20°$ and $200°$ C.

The reactions are preferably carried out at atmospheric pressure, although higher or lower pressures can be used.

If an acid acceptor is used this may also act as solvent. In addition to acid acceptors, suitable solvents or their mixtures, include optionally chlorinated aliphatic and aromatic hydrocarbon, such as cyclohexane, petroleum ether, benzene, toluene, xylene, dichloromethane, chloroform, carbon tetrachloride, 1,2-dichloroethane and chlorobenzene; ethers, such as for example diethyl ether, methyl ethyl ether, diisopropyl ether, dibutyl ether, propylene oxide, dioxane and tetrahydrofuran; ketones, such as acetone, methyl ethyl ketone and methyl isobutyl ketone and methyl isopropyl ketone; nitriles, such as acetonitrile, propionitrile and benzonitrile; esters, such as ethyl acetate and amyl acetate; amides, such as dimethylformamide and dimethylacetamide, as well as sulphones and sulphoxides, such as dimethyl sulphoxide and sulpholane.

Conventional basic materials are suitable as acid acceptors for reaction varaints a), i) and k), such as for example aliphatic, aromatic and heterocyclic amines, e.g. triethylamine, dimethylamine, pyridine and dimethylaminopyridine and inorganic bases such as oxides, carbonates, hydogen carbonates and alcoholates of alkali and alkaline earth metals, such as potassium hydroxide, sodium hydroxide and sodium and potassium carbonate.

Suitable catalysts for carrying out the reactions of process variants b), c), h), j) and l) are those which can bind the water that has formed. Especially suitable for the esterification is the binding of water by a combination of triphenylphosphine and an azodicarboxylate ester (Synthesis 1981, 1). Suitable also however are the classic dehydrating agents such as concentrated sulphuric acid, anhydrous salts of inorganic acids, such as magnesium sulphate or calcium chloride, carbodiimides, such as dicyclohexylcarbodiimide, and zeolites.

The halogenated $C_1$ units used in process variant c), j), k) and f) are well-known in the art (eg G. A. Wheaton; D. J Burton; J. Org. Chem 48, 917–927 (1983); D. J. Burton; J. Fluorine Chem. 23, 339–357 (1983); S. A. Fugua; W. G. Duncan; R. M. Silverstein; J. Org. Chem. 30, 2543–45 (1965)). Examples of halomethanes are $CCl_2F_2$, $CBr_2F_2$ and $CCl_3F$; of alkaline metal salts of trihalogenated acetic acids are $CClF_2CO_2Na$ and $CCl_2FCO_2Na$; and of trisubstituted phosphines $P(C_6H_5)_3$, $P(C_2H_5)_3$, $P(N(C_2H_5)_2)_3$ and $P(N(CH_3)_2)_3$. Oxidising agents for carrying out the reaction of process variant d) are those which are suitable for oxidising primary alcohols to acids. Examples are chromic acid, nitric acid and permanganate.

Examples of mono- and multivalent metals under the term M in process variant l) are for example alkali- and alkaline earth metals, silver, zinc, tin, mercury, copper, manganese etc.

As reducing agents for carrying out the reaction of process variant m) are all those which are suitable for selectively reducing an organic acid, containing an olefinic double bond, to an aliphatic alcohol. Examples include lithium aluminium hydride and isobutyl aluminium hydride.

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by fractional distillation or crystallisation.

The compounds of the invention are, as a rule, almost colourless and odourless liquids, that are almost insoluble in water and but are highly solubile in aliphatic hydrocarbons, such as hexane, halogenated hydrocarbons, such as chloroform, methylene chloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, sulphoxides, such as dimethyl sulphoxide.

The compounds of the invention are, as a rule, colourless oils that are highly soluble in practically all organic solvents but are almost insoluble in water.

The starting materials to the haloalkenes of formula II and III are known or can be prepared by well known methods.

The compounds of the invention demonstrate a good technical advance through good insecticidal and acaricidal activity. As a result of their activity against a wide range of sucking arthropods, the compounds of the invention can be used not only against plant pests but also for combating parasites of humans and domestic animals. In plants it is not necessary for the pests to be treated directly; it is usually sufficient to treat the plants on which they feed. The compounds are especially useful against parasites which have developed resistance to other substances.

Examples of insects, including animal ectoparasites, that can be combated by the compounds of the invention include Lepidoptera, such as *Plutella xylostella, Spodoptera littoralis, Heliothis armigera* and *Pieris brassi-* cae; Diptera, such as *Musca domestica, Ceratitis capitata, Erioischia brassicae, Lucilia sericata* and *Aedes aegypti;* Homoptera, including aphids such as *Megoura viciae* and *Nilaparvata lugens;* Coleoptera, such as *Phaedon cochleariae, Anthonomus grandis* and corn rootworms (Diabrotica spp. eg. *Diabrotica undecimpunctata*); Orthoptera, such as *Blattella germanica;* ticks, such as *Boophilus microplus* and lice, such as *Damalinia bovis* and *Linognathus vituli*, as well as mites such as *Tetranychus urticae* and *Panonychus ulmi.*

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts. Formulations can be prepared, for example, from the following ingredients.

A WETTABLE POWDER 20 percent by weight active ingredient
35 percent by weight bentonite
8 percent by weight calcium lignosulphonate
2 percent by weight of the sodium salt of N-methyl-N-oleyltaurine
35 percent by weight silicic acid

B PASTE 45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water

C EMULSIFIABLE CONCENTRATE 20 percent by weight active ingredient
75 percent by weight isophorone
5 percent by weight of a mixture of the sodium salt of N-methyl-N-oleyltaurine and calcium lignosulphonate The following examples illustrate the preparation of compounds according to the invention.

EXAMPLE 1

Process variant c)

Benzyl 6,6-difluoro-5-methyl-5-hexenoate 27.85 g Tris(dimethylamino)phosphine was added dropwise to a solution of 17.90 g dibromodifluoromethane in 130 ml diglyme, maintained under a nitrogen atmosphere and ice bath cooling. After stirring for one hour on the ice bath, 8.82 g benzyl 5-oxohexanoate in 70 ml diglyme was added slowly, dropwise. The ice bath was then removed and the reaction mixture stirred for 3 hours at room temperature, allowed to stand overnight, poured into 200 ml ice water and extracted with ether. The ether phase was washed twice with water, dried over sodium sulphate, filtered and concentrated in a rotary evaporator. The residue was distilled under reduced pressure.

Yield 8.78 g (86%)
bp=145°-152° C./18 mbar
$R_f$=0.50 (hexane ethyl/ethyl acetate=8/2)
$n_D^{20}$=1.4760

Preparation of the starting material

Benzyl 5-oxohexanoate 3.27 g (0.628 mol) Anhydrous potassium carbonate and a spatula full of sodium iodide was added to a solution of 50 g (0.385 mol) 5-oxohexanoic acid and 45.87 ml (0.385 mol) benzyl bromide in 380 dimethylformamide. After stirring for one hour at 100° C., the solvent was evaporated in a rotary evaporator. The residue was diluted with 250 ml water and extracted with ether. The ether phase was washed until it was neutral and concentrated.

Yield 81.28 g (95.9%)
$R_f$=0.50 (hexane/ethyl acetate=1/1)
The product was used without further purification.

Example 2

Process variant f)

3-Phenoxybenzyl 6,6-difluoro-5-methyl-5-hexenoate

A solution of 1.75 g 6,6-difluoro-5-methyl-5-hexanenitrile see Example 23) and 2 42 g 3-phenoxybenzyl alcohol in 15 ml absolute ether was saturated at 5° C. with HCl and stirred at 3° C. for 6 hours. After standing for 14 hours at room temperature, the mixture was treated with 50 ml water and brought to pH 4.5 with 10% aqueous sodium hydroxide. The ether was then distilled over 1 hour under reflux. 100 ml hexane was then stirred in and the separated organic phase washed twice with 100 ml water. After drying over calcium chloride and evaporation of the solvent in vacuo, the remaining residue was purified by column chromotography (silica gel; ethyl acetate/hexane=1/20).

Yield: 1.96 g (47%)
$R_f$=0.73 (ethyl acetate) $n_D^{22.4}$=1.52332

Example 3

6,6-Difluoro-5-methyl-5-hexanoic acid 1.27 g of the product of Example 1 was added to a solution of 0.36 g potassium hydroxide and 2 ml methanol. After stirring for two hours at room temperature, the reaction mixture was poured into water and treated with 5 ml 1N aqueous sodium hydroxide. The mixture was then washed 4 times with ethyl acetate. The aqueous phase was acidified with dilute hydrochloric acid and extracted with ethyl acetate. The organic phase was washed with saturated aqueous sodium chloride, dried over sodium sulphate and concentrated.

Yield: 0.70 g (85.3%)
$R_f$=0.47 (Hexane/ethyl acetate=1/1)
$n_D^{20}$=1.4057

Example 4

6,6-Difluoro-5-methyl-5-hexenoyl chloride 4.09 ml (56.29 mmol) Thionyl chloride was added dropwise to 3.50 g (21.32 mmol) of the product of Example 3 at room temperature. A drop of dimethylformamide was then added and the mixture heated for 6 hours under reflux. It was then distilled under reduced pressure.

Yield: 2.64 g (68%)
bp: 56°-59° C./26 mbar

Example 5

Process variant b)

1-Pyrrolidinylcarbonylmethyl 6,6-difluoro-5-methyl-5-hexenoate

A solution of 0.82 g (5 mmol) of the product of Example 3 and 0.6 g (5 mmol) N-(bromoacetyl)pyrrolidine in 5 ml dimethylformamide was treated at room temperature with 0.1 g sodium iodide and 0.7 ml (5 mmol) triethylamine and the mixture stirred for 10 hours at room temperature. The mixture was poured into 50 ml water and extracted 3 times with ethyl acetate. The combined ethyl acetate phase was washed with 2% aqueous sodium hydrogen carbonate and then with water, dried over sodium sulphate and concentrated. The crude product was purified by column chromatography on silica gel with hexane/ethyl acetate 1:1 as eluent and a sample tested by TLC with ethyl acetate as eluent, ($R_f$=0.26).

Yield: 0.74 g (54%)
$n_D^{20}$=1.4667

Example 6

Process variant m)

6,6-Difluoro-5-methyl-5-hexane-1-ol 1 50 mg (3.95 mmol) Lithium aluminium hydride was added, portionwise, to a solution of 0.4 g (2.44 mmol) of the product of Example 3 in 20 ml ether. After stirring for 1 hour under reflux, excess lithium aluminium hydride was decomposed by the addition of water. The solid was filtered off and washed with water. The filtrate was washed with water, dried over sodium sulphate, filtered and concentrated on a rotary evaporator. The residue was purified by column chromatography (silica gel; hexane: ethyl acetate=8.2).

Yield: 330 mg (90%)
$n_D^{23.13}$=1.4172
$R_f$=0.39 (hexane/ethyl acetate=1/1)

Example 7

Process variant i)

6,6-Difluoro-5-methyl-5-hexenyl 4-butoxybenzoate

A solution of 468 mg (2.2 mmol) 4-n-butoxybenzoyl chloride in 5 ml tetrahydrofuran was added dropwise at 0° C. to a solution of 330 mg (2.2 mmol) of the product of Example 6 in 10 ml triethylamine. After stirring for 16 hours at room temperature, the reaction mixture was filtered through kiselguhr, the filtrate poured into 15 ml ice/water and extracted with ether. The organic phase was dried over sodium sulphate, filtered and concentrated. The residue was purified by column chromatography (silica gel; hexane:ethyl acetate=4.1).

Yield: 0.66 g (2.02 mmol)=92%
$n_D^{20}$=1.4925
$R_f$=0.69 ethyl acetate

Example 8

Process variant c)

Methyl 6,6-difluoro-5-hexenoate

A solution of 92.17 g (0.61 mmol) sodium chlorodifluoroacetate in 200 ml diglyme was added dropwise slowly to a solution of 39.87 g (0.306 mmol) methyl 5-oxopentanoate (Schreiber et al, Tet. Lett., 23 3867-3870 (1982)) and 90.15 g (0.37 mol) triphenylphosphine in 75 ml diglyme at 160° C. The mixture was then stirred for 2 hours at 160° C. and stirred overnight at room temperature. It was then poured into 2 L water and extracted 4 times with ether. The combined ether phase was washed twice with water, dried over sodium sulphate, filtered and concentrated in a rotary evaporator. The residue was purified by column chromatography (silica gel; hexane/ethyl acetate=8/2)

Yield: 19.8 g (39%)
$R_f$=0.39 (hexane:ethyl acetate=8:2
$n_D^{20}$=1.4067

Example 9

6,6-Difluoro-5-hexenoic acid

A solution of 6 g (106.9 mmol) KOH flakes and 19.0 g (120.6 mmol) of the product of Example 8 in 50 ml methanol was stirred at room temperature overnight. The mixture was then concentrated on a rotary evaporator. The residue was dissolved in 40 ml water and washed twice with ether. The aqueous phase was acidified with 1N hydrochloric acid and extracted 4 times with ether. The ether phase was washed with water, dried over sodium sulphate, filtered and concentrated in a rotary evaporator.

Yield: 15.3 g (84.5%)
$R_f$=0.45 (hexane/ethyl acetate=1/1)
$n_D^{20}$=1.4048

Example 10

6,6-Difluoro-5-hexenoyl chloride 10.23 ml (140.68 mmol) Thionyl chloride was added dropwise to 8.0 g (52.29 mmol) of the product of Example 9 at room temperature. A drop of dimethylformamide was added and the mixture heated under reflux for 6 hours. It was then distilled under reduced pressure.

Yield 6.6 g 73.5%)
bp=52°-54° C./36 mbar

Example 11

2-Naphthylmethyl 6,6-difluoro-5-hexenoate

A solution of 0.83 ml (5 mmol) diethyl azodicarboxylate was added, dropwise, slowly, at room temperature to a solution of 0.75 g (5 mmol) of the product of Example 9, 0.79 g (5 mmol) 2-Naphthylmethanol and 1.34 g (5.1 mmol) triphenylphosphine in 15 ml tetrahydrofuran. After stirring for 6 hours at room temperature, the reaction mixture was concentrated in a rotary evaporator. The crude product was purified by column chromatography (silica gel; hexane: ethyl acetate=8.2).

Yield: 0.89 g (61%)
$R_f$=0.25 (Hexane:toluene—1:1)
$n_D^{20}$=1.5408

Example 12

Process variant a)

Methyl N-(6,6-difluoro-5-hexen-1-oyl)-L-phenylalaninate 0.84 g (5 mmol) 6,6-Difluorohex-5-enoyl chloride was added, dropwise, slowly, to a solution of 1.08 g (5 mmol) methyl L-phenylalaninate hydrochloride and 0.1 g 4-dimethylaminopyridine in 20 ml pyridine under ice-bath cooling. After stirring for 16 hours at room temperature, the reaction mixture was poured into 20 ml ice-water and extracted with ethyl acetate. The organic phase was washed once with 20 ml water, dried over sodium sulphate, filtered and concentrated on a rotary evaporator. The residue was purified by column chromatography (silica gel; hexane: ethyl acetate=1:1).

Yield: 1.40 g (94%)
$R_f$=0 21 (Hexane:ethyl acetate=1:1)
$n_D^{20}$=1.4965

Example 13

Process variant j)

1-Benzoyloxy-6,6-difluoro-5-hexene 3.6 ml (20 mmol) Tris(dimethylamino)phosphine was added, dropwise, with icebath cooling to a solution of 0.93 ml 10 mmol) dibromodifluoromethane in 20 ml diglyme. After stirring for 90 minutes at 0° C., a solution of 1.0 g (4.9 mmol) 5-benzyloxyvaleraldehyde in 10 ml diglyme was added dropwise and the mixture stirred overnight at room temperature. The colourless precipitate was filtered off and washed with 10 ml diglyme. The filtrate was concentrated in a rotary evaporator and the residue purified by column chromatography (silica gel; hexane:ethyl acetate=1:1).

Yield 1.0 g (85%)
$R_f$=0.75 (ethyl acetate)
$n_D^{20}$=1.4815

Preparation of the Starting Material

1-Benzoyloxypentan-5-ol

A solution of 47 ml (0.5 mol) benzoyl chloride in 100 mol tetrahydrofuran was added dropwise slowly to a solution of 40 g (0.39 mol) 1,5-pentanediol in 500 ml tetrahydrofuran and 58 ml (0.42 mol) triethylamine. After stirring for 14 hours at room temperature, the reaction mixture was concentrated in a rotary evaporator. The residue was purified by column chromatography (silica gel; hexan:ethyl acetate=2:1).

Yield: 35.8 g (45%)
$R_f$=0.62 (ethyl acetate)

5-Benzoyloxyvaleraldehyde 2.2 ml (31 mmol) Dimethyl sulphoxide was added over 10 minutes, dropwise, to a solution of 1.55 ml (18 mmol) oxalyl chloride in 40 ml dichloromethane, maintained at −60° C. under a nitrogen atmosphere. After stirring for 30 minutes at −60° C., 2.1 g (10 mmol) 1-benzoyloxypentan-5-ol was added dropwise and the mixture stirred for 30 minutes at −60° C. At this temperature, 11.3 ml (82 mmol) triethylamine was added dropwise over 15 minutes. The reaction mixture was warmed to room temperature, treated with 20 ml water and extracted with dichloromethane. The organic phase was dried over sodium sulphate, filtered and concentrated in a rotary evaporator. The reaction product was used without further purification.

Yield: 2.02 g (98%)
$R_f$=0.46 (toluene: ethyl acetate=4:1)

Example 14

6,6-Difluoro-5-hexene-1-ol 0.6 g (11 mmol) Sodium methanolate was added to a solution of 2.4 g (10 mmol) of the product of Example 13. After stirring for 2 hours at room temperature, the solvent was removed in a rotary evaporator. The residue was dissolved in 20 ml water and extracted with ether. The ether phase was concentrated in a rotary evaporator and the residue distilled under reduced pressure.

Yield: 0.33 g (24%)
bp=75°-80° C./35 mbar
$n_D^{20}$=1.400

Example 15

Process variant i)

6,6-Difluoro-5-hexenyl 4-butoxybenzoate

A spatula full of 4-dimethylaminopyridine was added to a solution of 1 g (7.4 mmol) of the product of Example 14 in 25 ml tetrahydrofuran and 1.2 ml (8.5 mmol) triethylamine. Then under ice-bath cooling, a solution of 1.6 g (7.4 mmol) 4-butoxybenzoyl chloride in 5 ml THF was added dropwise slowly and the mixture stirred at room temperature for 6 hours. The reaction product was poured into 20 ml ice-water and extracted with ethyl acetate, dried with sodium sulphate, the extract filtered and concentrated in a rotary evaporator. The residue was purified by column chromatography (silica gel; hexane/ethyl acetate=3:1).

Yield: 2.0 g (87%)
$R_f$=0.75 (ethyl acetate)
$n_D^{20}$=1.4920

Example 16

Process variant e)

5,6,6-Trifluoro-5-hexanoic acid

A solution of 6.70 g (28.34 mmol) 2-(3,4,4-trifluoro-3-butenyl)malonic acid in 40 ml xylene was heated for 8 hours under reflux. After cooling the mixture was diluted with 100 ml ether and extracted 3 times with 50 ml 1N aqueous sodium hydroxide. The aqueous phase was washed with 50 ml ether and then acidified with dilute hydrochloric acid. It was then extracted 4 times with 50 ml ether each time. The combined ether extract was washed with aqueous sodium chloride, dried over sodium sulphate, filtered and concentrated. The residue was used without further purification.

Yield: 3.36 g (70.10%
R_f=0.55 (ethyl acetate)

Preparation of the Starting Material

Dibenzyl 2-(3,4,4-trifluoro-3-butenyl)malonate 10.9 g (100.8 mmol) Benzyl alcohol was added slowly dropwise to a suspension of 3.18 g (105.8 mmol) 80% sodium hydride in white oil in 100 ml THF. The mixture was then heated under reflux for 1 hour. 28.66 g (100.8 mmol) Benzyl malonate was added then added dropwise at 50° C. After stirring for 1 hour 20 g (105.8 mmol) 4-bromo-1,1,2-trifluoro-1-butene was added dropwise. The reaction mixture was stirred overnight at room temperature and then heated at reflux for a further 4 hours. After cooling, the reaction mixture was poured into 100 ml ice-water and extracted with ethyl acetate. The ethyl acetate phase was washed neutral, dried over sodium sulphate, filtered and concentrated in a rotary evaporator. The residue was purified by column chromatography (silica gel; hexane/ethyl acetate=4:1).

Yield: 12.01 g (29%)
R_f=0.32 hexane: ethyl acetate=8:2)
$n_D^{20}$=1.5106

2-(3,4,4-Trifluoro-3-butenyl)malonic acid 5.56 g (99 mmol) KOH flakes were dissolved in 6.82 ml water and 13.65 ml ethanol and then treated with 11.12 g (28.34 mmol) of dibenzyl 2-(3,4,4-trifluoro-3-butenyl)-malonate. After heating under reflux for 4 hours, the reaction mixture was poured into 30 ml water and washed with ether. The aqueous phase was acidified with dilute hydrochloric acid and extracted 4 times with ether. The organic phase was dried over sodium sulphate, filtered and then concentrated in a rotary evaporator.

Yield: 5.95 g (99%)
The product was used without further purification.

Example 17

Process variant b)

3-Phenoxybenzyl 5,6,6-trifluoro-5-hexenoate

A solution of 0.83 ml (5 mmol) Diethyl azodicarboxylate in 10 ml THF was added, dropwise, slowly to a solution of 0.84 g (5 mmol) 5,6,6-trifluoro-5-hexenoic acid, 1.0 g (5 mmol) 3-phenoxybenzyl alcohol and 1.34 g (5 mmol) triphenylphosphine in 15 ml tetrahydrofuran at room temperature. After the mixture had been stirred for 6 hours at room temperature, it was concentrated in a rotary evaporator. The crude product was purified by column chromatography (silica gel; hexane: toluene=1,1).

Yield: 41%
R_f=0.19 (hexane/toluene=1:1)
$n_D^{20}$=1.5207

Example 18

Process variant c)

2-Naphthylmethyl 6,6-difluoro-5-phenyl-5-hexenoate 4.82 ml (25.5 mmol) Tris(dimethylamino)phosphine in 20 ml diglyme was added dropwise slowly at 0° C. to a solution of 2.68 g (12.75 mmol) dibromodifluoromethane in 20 ml diglyme. After stirring for 1 hour at 0° C., a solution of 2 g (6.02 mmol) 2-naphthylmethyl 4-benzoylbutyrate in 10 diglyme was added dropwise. After stirring overnight at room temperature, the reaction mixture was filtered, the filtrate concentrated in a rotary evaporator and purified column chromatography (silica gel; hexane/ethyl acetate =8:2).

Yield: 1.47 g (67.2%)
$n_D^{21.3}$=1.5651
R_f=0.42 (hexane/methyl acetate=8:2)

Preparation of the Starting Material

2-Naphthylmethyl 4-benzoylbutyrate 2.89 ml (15.56 mmol) Diethyl azodicarboxylate was added slowly, dropwise, to a solution of 3 g (15.61 mmol) benzoylbutyric acid, 2.47 g (15.61 mmol) 2-naphthylmethanol and 4.0 g (15.56 mmol) triphenylphosphine in 50 ml tetrahydrofuran at room temperature. After stirring for 6 hours at room temperature, the reaction mixture was concentrated in a rotary evaporator and the residue purified by column chromatography (silica gel; hexane/acetic acid=8:2).

Yield: 4.6 g (89%)
R_f=0.24 (hexane/ethyl acetate=8:2)
$n_D^{21.3}$=1.5965

Example 19

Process variant i)

6,6-Difluoro-5-trifluoromethyl-5-hexenyl 4-butoxybenzoate

A solution of 0.76 ml (4.0 mmol) 4-butoxybenzoyl chloride in 7 ml tetrahydrofuran was added dropwise to a solution of 0.82 g (4.0 mmol) 6,6-difluro-5-trifluoromethyl-5-hexene-1 ol in 10 ml tetrahydrofuran and 0.61 ml (4.4 mmol) triethylamine ar 0° C. After stirring for 16 hours at room temperature, the reaction mixture was filtered on kieslguhr. The filtrate was poured into 15 ml ice-water and extracted with ether. The organic phase was dried over sodium sulphate, filtered and concentrated. The residue was purified by column chromatography (silica gel; hexane; ethyl acetate=9:1)

Yield 0.68 g (45%)
$n_D^{20}$=1.4660
R_f=0.65 (ethyl acetate=8:2)

Preparation of the Starting Material

4-Chloro-1-tert-butyldimethylsilyloxybutane

A solution of 40.17 g (370 mmol) 4-chlorbutanol, 25.19 g (370 mmol) imidazole and 55.77 g (370 mmol) tert-butyldimethylsilyl chloride in 220 ml dimethylformamide was stirred at room temperature for 16 hours. The reaction mixture was then poured into 150 ml 5% aqueous ammonium chloride and extracted 4 times, each time with 200 ml of ether. The combined ether phases were washed 4 times with 200 ml water, dried over sodium sulphate, filtered and concentrated. The residue was purified by column chromatography (silica gel; hexane/ethyl acetate=9:1)

Yield: 67 g (81%)
R_f=0.68 (ethyl acetate)

4-Trifluoro-1-tert-butyldimethylsilyloxybutane

A solution of 4.14 ml (54 mmol) trifluoroacetic acid in 20 ml tetrahydrofuran was added dropwise slowly to a solution of 4-tert-butyldimethylsilyoxybut-1-ylmagnesium chloride [prepared from 36.11 g (162 mmol) 4-chloro-1-tert-butyldimethylsilyloxybutane and 4.21 g (170 mmol) magnesium turnings] in 300 ml tetrahydrofuran. The reaction mixture was heated under reflux for 1 hour, allowed to stand at room temperature overnight and poured into ice-water containing dilute hydrochloric acid. After extraction with ether, the organic phase was washed with ¼ saturated aqueous sodium chloride, dried over sodium sulphate, filtered and concentrated. The residue was purified by column chromatography (silica gel; hexane/ethyl acetate=9:1)

Yield: 12.5 g (47 mmol) 86%
$R_f$=0.36 (hexane/ethyl acetate =8:2)

6,6-Difluoro-5-trifluoromethyl-1-tert-butyldimethylsilyloxy-5-hexene

A solution of 12.88 g (85.7 mmol) sodium chlorodifluoroacetate in 30 ml diglyme was added dropwise slowly to a solution of 11.50 g (42.9 mmol) 4-trifluoroacetyl-1-tert-butyldimethylsilyloxybutane and 12.54 g (47 mmol) triphenylphosphine in 30 ml diglyme at 165° C. The mixture was heated for one hour under reflux. After cooling, the crude product was distilled at high vacuum. The distillate which contained diglyme and reaction product was poured into 200 ml water and extracted 4 times, each time with 100 ml ether. The combined ether phases were washed 3 times, each time with 100 ml water, dried over sodium sulphate, filtered and concentrated. The crude product was purified by column chromatography (silica gel; hexane/ethyl acetate=9:1).

Yield: 6.52 g (48%)
$R_f$=0.72 (ethyl acetate)

6,6-Difluoro-5-trifluoromethyl-5-hexenol

A solution of 3.59 g (11.28 mmol) 6,6-difluoro-5-trifluoromethyl-1-tert-butylsilyloxy-5-hexene in 50 ml methanol was treated with a teaspoon full of ion exchange resin and the mixture stirred for 3 hours at room temperature. The ion exchange resin was then filtered off and washed with methanol. The filtrate was carefully concentrated in a rotary evaporator (bath temperature=35° C.; 200 mbar). The residue was used without further purification.

Example 20

Process variant b)

Hexadecyl 5-bromo-(6,6-difluoro-5-hexenoate)

A solution of 0.8 g (1.5 mmol) hexadecyl 5,6 dibromo-6,6-difluorohexanoate and 0.23 g (1.5 mmol) 1,8-diazabicyclo[5.4.0]undec-7-ene in 50 ml dichloromethane was stirred for 4 hours at room temperature. The reaction mixture was poured into 30 ml water and extracted with dichloromethane. The organic phase was dried over sodium sulphate, filtered and concentrated. The residue was purified by column chromatography (silica gel; hexane/ethyl acetate=9:1).

Yield: 0.68 g (93%)
$n_D^{23.4}$=1.45328
$R_f$=0.79 (ethyl acetate)

Preparation of the Starting Material

Hexadecyl 5,6-dibromo-6,6-difluorohexanoate

A solution of 0.54 ml (10.36 mmol) bromine in 10 ml dichloromethane was added dropwise to a solution of 1.94 g (5.18 mmol) hexadecyl 6,6-difluoro-5-hexenoate ester in 15 ml ether at 0° C. After heating under reflux for 6 hours, the mixture was poured in 100 ml 10% aqueous sodium thiosulphate and extracted with ether. The organic phase was washed with water, dried over sodium sulphate, filtered and concentrated. The residue was purified by column chromatography (silica gel; hexane/ethyl acetate=9:1).

Yield: 1.65 g (60%)
$n_D^{20}$=1.46768
$R_f$=0.69 (hexane/ethyl acetate=7:3)

Example 21

Process variant i)

5-Chloro-6,6-difluoro-5-hexenyl 2,4-difluorobenzoate

A solution of 0.7 g (2 mmol) 5,6-dichloro-6,6-difluoro-5-hexyl 2,4-difluorobenzoate in 10 ml dichloromethane was heated under reflux for 8 hours. The reaction mixture was concentrated and the residue purified by column chromatography (silica gel hexane/ether=4:1).

Yield: 0.4 g (64%) $n_D^{20}$=1.4743
$R_f$=0.72 (ethyl acetate)

Preparation of the Starting Material 5,6-Dichloro-6,6-difluoro-5-hexyl 2,4-difluorobenzoate Chlorine gas was passed into a solution of 1.4 g (5.1 mmol) 6,6-difluoro-5-hexenyl 2,4-difluorobenzoate in 20 ml chloroform at −35° to −20° C. over 40 minutes and the mixture was then stirred for 2 hours at room temperature. The reaction mixture was concentrated and the residue purified by column chromatography (silica gel; hexane/ether=1:1)

Yield: 1.5 g (84%)
$n_D^{20}$=1.4747
$R_f$=0.72 (ethyl acetate)

Example 22

Process variant b)

Benzyl 8,8-difluoro-7-methyl-7-octenoate 123 ml (0.68 mol) Tris(dimethylamino)phosphine in 100 ml diglyme was added slowly dropwise to a solution of 26.3 ml (0.34 mol) dibromodifluoromethane in 800 ml diglyme. After stirring for one hour on an ice bath, 43 g (0.17 mol) benzyl 7-oxooctanoate in 100 ml diglyme was slowly added dropwise. The ice bath was removed and the reaction mixture stirred for 40 minutes at room temperature, poured into 1 liter ice-water and extracted with ether. The ether phase was washed twice with water, dried over sodium sulphate, filtered and concentrated. The residue was purified by column chromatography (silica gel hexane/ether=3:1)

Yield: 32.5 g (68%)
$n_D^{20}$=1.4759

Preparation of the Starting Material

Benzyl 7-oxooctanoate

Benzyl 7-oxooctanoate was prepared by benzylation of 7-oxooctanoic acid with benzyl bromide and potassium carbonate in dimethyl formamide.

7-Oxooctanoic acid

7-Oxooctanoic acid was prepared by treatment of 2-acetyl cyclohexanone with aqueous potassium hydroxide (S. Hünig et al; Chem Ber 91, 129–133 (1958)).

Example 23

Process variant f)

6,6-Difluoro-5-methyl-5-hexenitrile 65.9 g Tris(dimethylamino)phosphine was added dropwise to a solution of 42.4 g dibromodifluormethane in 350 ml tetrahydrofuran at 0° to 5 C. The mixture was heated over 2 hours to 20° C., cooled to −20° C., and then treated, dropwise, with a mixture of 15.7 g 5-oxohexanenitrile and 10 ml tetrahydrofuran The mixture was then stirred at 0° C. for 2 hours and allowed to stand for 12 hours at room temperature. The reaction mixture was poured into 1000 ml water and extracted 3 times with 500 ml n-hexane. After drying the combined organic phases over magnesium sulphate, the solvent was distilled off under slightly reduced pressure and the residue fractionally distilled in vacuo.

Yield 13.3 g (65%)

bp: 36° C.

In a similar manner the following compounds were prepared

| | | | | Phys. Const. | | |
|---|---|---|---|---|---|---|
| Expl. No. | process | E | $R^1$ | $n_D^{20}$ or | mp (°C.) | $R_F$ |

General formula $$\text{F}_2\text{C}=\text{C}(\text{CH}_3)-\text{CH}_2\text{CH}_2\text{CH}_2-\text{C}(=O)-E-R^1$$

| Expl. No. | process | E | $R^1$ | $n_D^{20}$ | mp (°C.) | $R_F$ |
|---|---|---|---|---|---|---|
| 24 | b) | O | 2-ethylnaphthyl | 1.5429 | | |
| 25 | b) | O | —C$_{16}$H$_{33}$ | 1.4386 | | |
| 26 | a) | —NH | H | | 57–57° C. | |
| 27 | a) | —NH | —CH$_2$—C≡C—H | | | |
| 28 | a) | —NH | 3,4-dichlorophenyl | 1.5427 | | |
| 29 | a) | —NH | —CH(CO$_2$Me)—CH$_2$—Ph | | | |
| 30 | a) | —NH | —CH$_2$—CO$_2$H | | 56–60° C. | |

General formula $$\text{F}_2\text{C}=\text{C}(\text{CH}_3)-\text{CH}_2\text{CH}_2\text{CH}_2\text{CH}_2-\text{O}-\text{C}(=O)-R^1$$

| Expl. No. | process | $R^1$ | $n_D^{20}$ | $R_F$ |
|---|---|---|---|---|
| 31 | m) | 4-(isopropoxy)phenyl | 1.4921 | 0.14 (Hexane/Toluene = 1/1) |
| 32 | m) | (F$_2$C=C(CH$_3$)-pentyl) | 1.4152 | |
| 33 | m) | styryl | | |
| 34 | m) | 4-(isopropoxy)styryl | | |
| 35 | m) | 4-(propargyloxy)styryl | 1.5468 | |

-continued
| | | | | |
|---|---|---|---|---|
| 36 | m) | 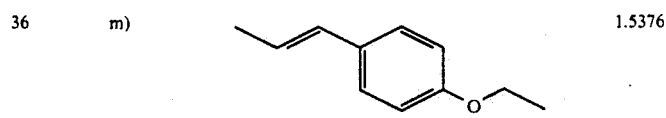 | | 1.5376 |
| 37 | m) | —C$_{16}$H$_{33}$ | | |
| 38 | m) | 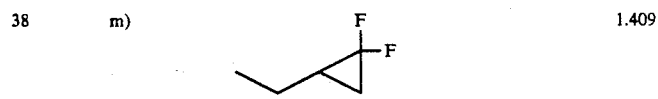 | | 1.409 |
| 39 | m) | 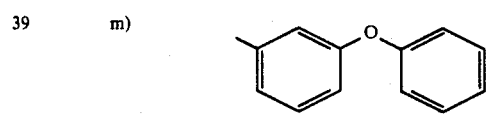 | | |
| 40 | m) |  | | |
General formula
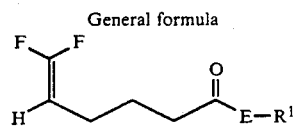
| | | | | |
|---|---|---|---|---|
| 41 | b) | O | 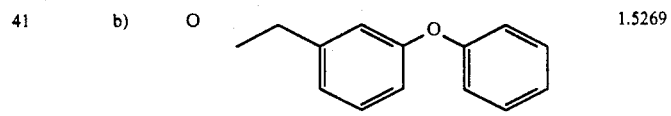 | 1.5269 |
| 42 | b) | O | —C$_{16}$H$_{33}$ | 1.4373 |
| 43 | b) | O | —C$_{18}$H$_{37}$ | |
| 44 | b) | O | —C$_{10}$H$_{21}$ | 1.4304 |
| 45 | b) | O | 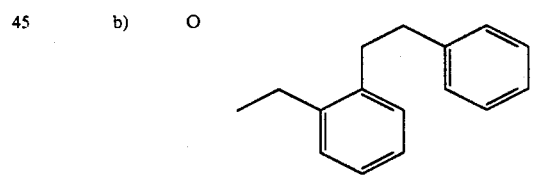 | |
| 46 | b) | O | 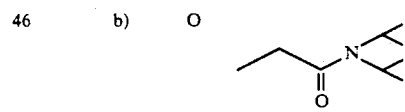 | |
| 47 | b) | O | 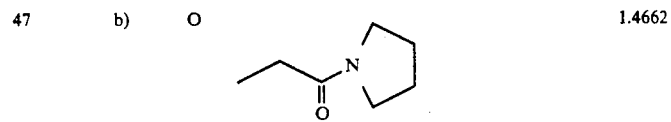 | 1.4662 |
| 48 | a) | —NH | H | 64–67° C. |
| 49 | a) | —NH | —CH$_2$—C≡C—H | 1.4524 |
| 50 | a) | —NH | 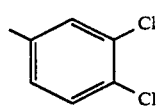 | 81–83° C. |
| 51 | a) | —NH | 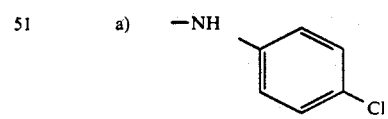 | |
General formula -continued
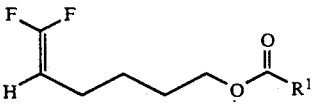
| | | R¹ | n²⁰_D |
|---|---|---|---|
| 52 | h) | 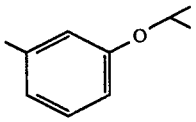 | 1.4921 |
| 53 | i) | 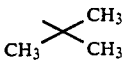 | 1.41194 |
| 54 | h) | —C₁₆H₃₃ | |
| 55 | h) |  | 1.5532 |
| 56 | h) | 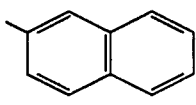 | 1.5296 |
| 57 | i) | 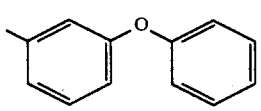 | 1.4581 |
| 58 | h) | 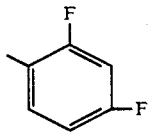 | 1.48808 |
| 59 | i) | 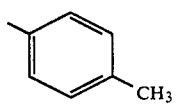 | 1.5475 |
| 60 | i) | 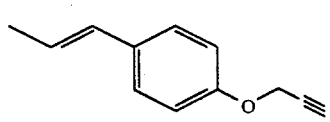 | 1.45408 |
| 61 | h) | 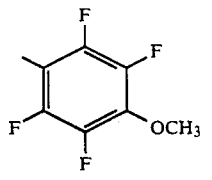 | 38–40° C. |
| 62 | i) | 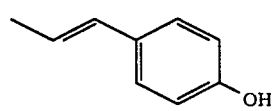 | 1.4740 |
| 63 | i) |  | 1.4990 |

-continued

| No. | Type | E | R¹ | n |
|---|---|---|---|---|
| 64 | i) | | 2,4-dichlorophenyl | 1.5128 |
| 65 | i) | | pentafluorophenyl | 1.4367 |
| 66 | i) | | 4-methoxyphenyl | 1.4997 |
| 67 | h) | | 4-tert-butylphenyl | 1.4895 |
| 68 | i) | | $-C_{17}H_{35}$ | 1.4620 |

General formula:

$$\text{CF}_2=\text{CF}-\text{CHF}-\text{CH}_2-\text{CH}_2-\text{C(=O)}-E-R^1$$

| No. | Type | E | R¹ | n |
|---|---|---|---|---|
| 69 | e) | O | benzyl | |
| 70 | b) | O | 2-naphthylmethyl | 1.53398 |
| 71 | e) | O | $-C_{16}H_{33}$ | 1.4366 |
| 72 | e) | O | $-C_{18}H_{37}$ | |
| 73 | e) | O | $-C_{10}H_{21}$ | |
| 74 | e) | O | 2-(2-phenylethyl)benzyl | 1.5188 |
| 75 | e) | O | $-CH_2-C(=O)-N(iPr)_2$ | |
| 76 | e) | O | $-CH_2-C(=O)-N(\text{pyrrolidinyl})$ | |
| 77 | e) | $-NH$ | H | |
| 78 | e) | $-NH$ | $-CH_2-C\equiv C-H$ | |
| 79 | e) | $-NH$ | 3,4-dichlorophenyl | |

-continued
| | | | |
|---|---|---|---|
| 80 | e) | —NH | 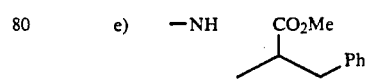 |
| 81 | e) | —NH | —CH₂—CO₂H |
General formula
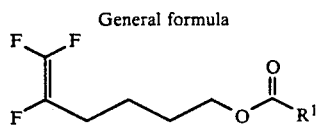
| | | |
|---|---|---|
| 82 | m) | Ph |
| 83 | m) | 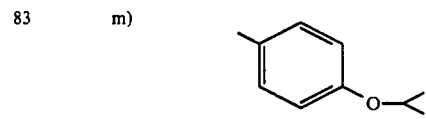 |
| 84 | m) | 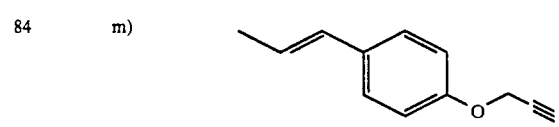 |
| 85 | m) | —C₁₆H₃₃ |
General formula
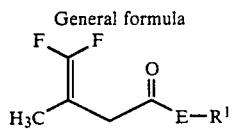
| | | | |
|---|---|---|---|
| 86 | d) | O | H |
| 87 | d) | O | 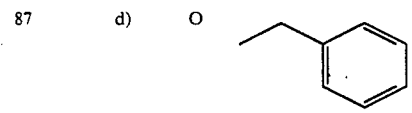 |
| 88 | d) | O | 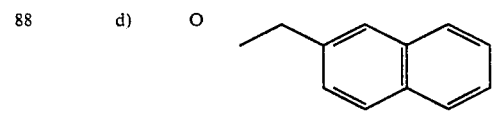 |
| 89 | d) | O | 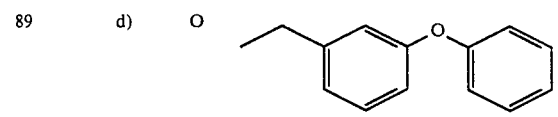 |
| 90 | d) | O | 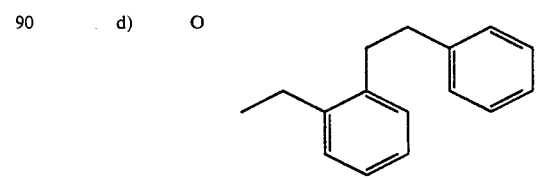 |
| 91 | d) | O | —C₁₆H₃₃ |
| 92 | d) | O | —C₁₈H₃₇ |
| 93 | d) | O | —C₁₀H₂₁ |
| 94 | d) | O | 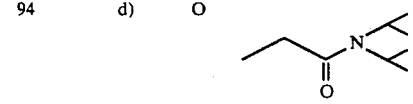 |
| 95 | d) | O | 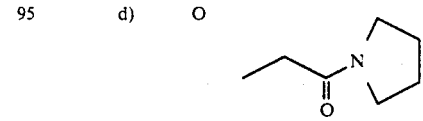 |

-continued
| | | | | |
|---|---|---|---|---|
| 96 | d) | —NH | H | |
| 97 | d) | —NH | —CH$_2$—C≡C—H | |
| 98 | d) | —NH | 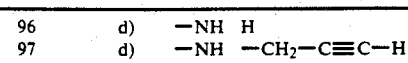 | |
| 99 | d) | —NH | —CH$_2$—CO$_2$H | |
| 100 | d) | —NH | 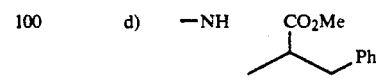 | |
General formula
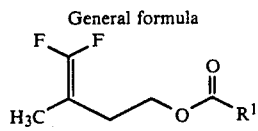
| | | | |
|---|---|---|---|
| 101 | i) |  | 1.4861 |
| 102 | i) |  | |
| 103 | i) | 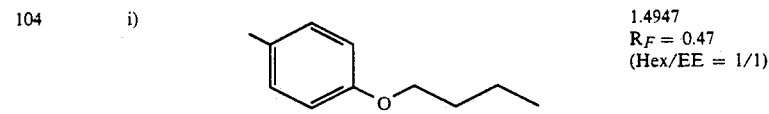 | |
| 104 | i) | 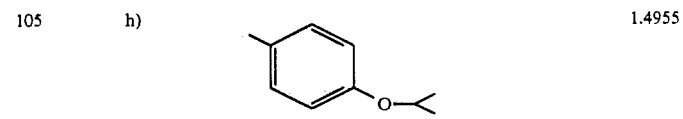 | 1.4947<br>R$_F$ = 0.47<br>(Hex/EE = 1/1) |
| 105 | h) | 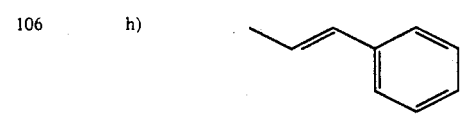 | 1.4955 |
| 106 | h) | 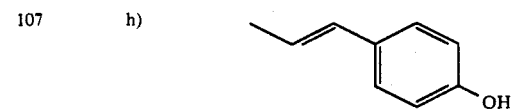 | |
| 107 | h) | 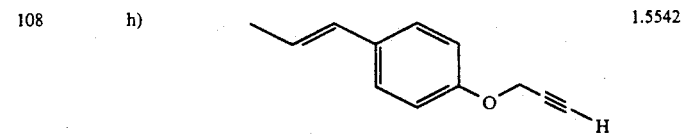 | |
| 108 | h) | 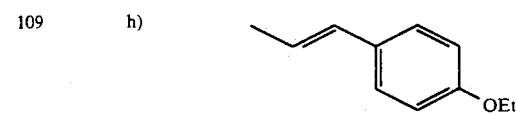 | 1.5542 |
| 109 | h) |  | |
| 110 | i) | —C$_{16}$H$_{33}$ | |
General formula -continued
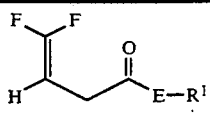
| | | | |
|---|---|---|---|
| 111 | d) | O | H |
| 112 | d) | O | —C₁₆H₃₃ |
| 113 | d) | O | —C₁₈H₃₇ |
| 114 | d) | O | 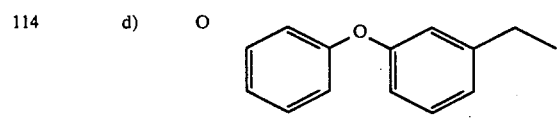 |
| 115 | d) | O | 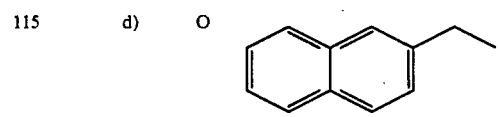 |
| 116 | d) | —NH | H |
| 117 | d) | —NH | —CH₂—CH₂—C≡CH |
| 118 | d) | —NH | 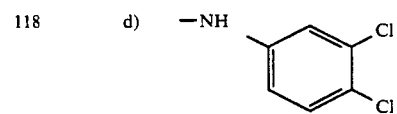 |
| 119 | d) | —NH | 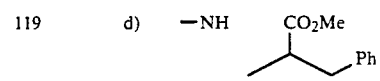 |
| 120 | d) | —NH | 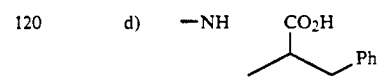 |
| 121 | d) | —NH | 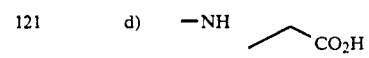 |
| 122 | d) | O | 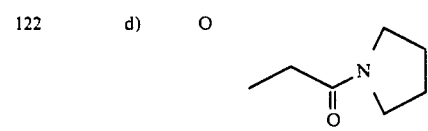 |
| 123 | d) | O | 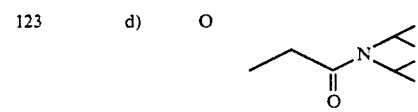 |
General formula
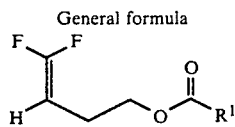
| | | |
|---|---|---|
| 124 | i) | 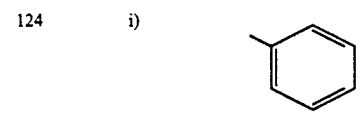 |
| 125 | i) |  |
| 126 | i) |  |

-continued
| | | | |
|---|---|---|---|
| 127 | i) | 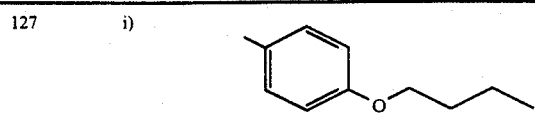 | |
| 128 | h) | 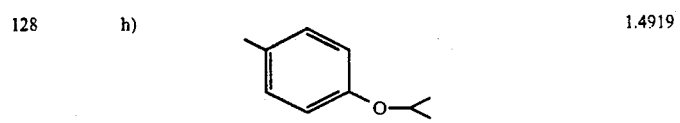 | 1.4919 |
| 129 | h) |  | |
| 130 | h) | 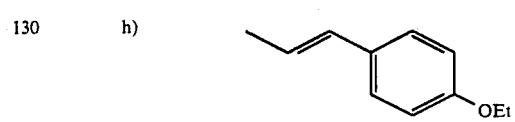 | |
| 131 | h) | 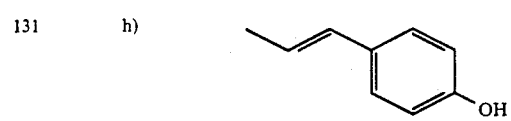 | |
| 132 | i) |  —C$_{16}$H$_{33}$ | |
General formula
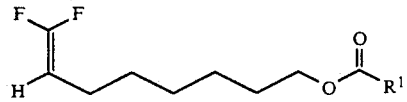
| | | | |
|---|---|---|---|
| 133 | h) | 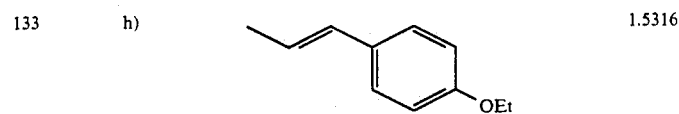 | 1.5316 |
| 134 | h) | 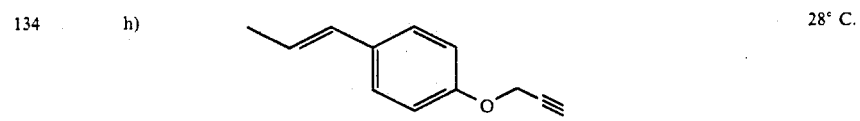 | 28° C. |
| 135 | i) | —CH$_3$ | 1.4103 |
| 136 | i) |  | 1.4942 |
| 137 | h) |  | 1.5244 |
| 138 | h) | 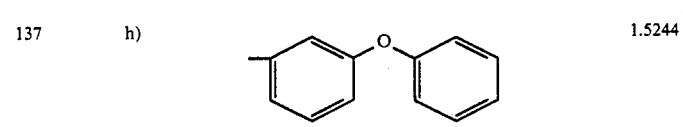 | 1.4874 |
| 139 | i) | 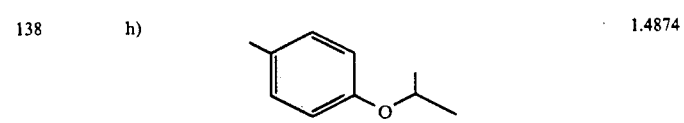 | 1.4762 |
General formula -continued
General formula:
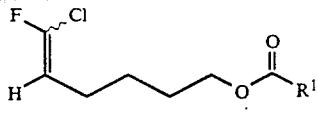
| | | | | |
|---|---|---|---|---|
| 140 | i) | |  | 1.5073 |
| 141 | i) | | 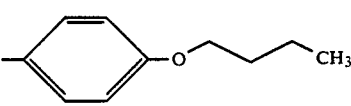 | 1.5109 |
| 142 | i) | | 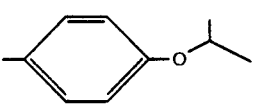 | 1.5120 |
General formula
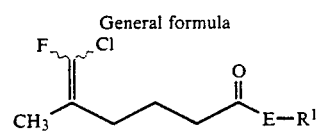
| | | | | |
|---|---|---|---|---|
| 143 | b) | O | 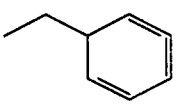 | 1.5058 |
| 144 | a) | O | H | 1.4501 |
| 145 | b) | O |  | 1.5613 |
| 146 | b) | O | 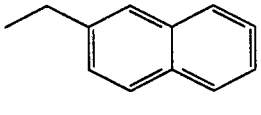 | 1.5430 |
| 147 | b) | O | —$C_{16}H_{33}$ | 1.4527 |
General formula
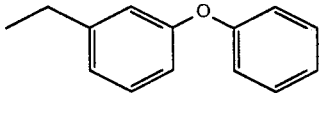
| | | | | |
|---|---|---|---|---|
| 148 | c) | O | H | |
| 149 | b) | O |  | 1.51962 |
| 150 | b) | O | —$C_{16}H_{33}$ | 1.44442 |
| 151 | b) | O | 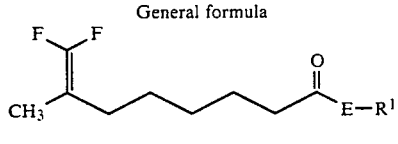 | 1.53522 |
| 152 | a) | —NH |  | 70° C. |

-continued
| Expl. No. | process | formula | | Phys. Const. $n_D^{20}$ or mp (°C.) | $R_F$ |
|---|---|---|---|---|---|
| 153 | a) | —NH | H | 82° C. | |
General formula
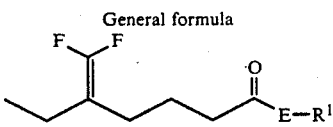
| 154 | c) | O | H | | 0.52*) |
| 155 | b) | O | 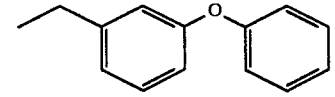 | 1.52406 | |
| 156 | b) | O | 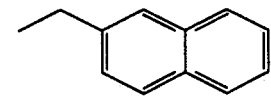 | 1.53678 | |
| 157 | b) | O | —C$_{16}$H$_{33}$ | 1.44414 | |
| 158 | a) | —NH | 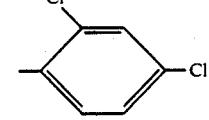 | 78° C. | |
| 159 | a) | —NH | H | 59° C. | |
| 160 | c) | O | —C$_2$H$_5$ | | 0.50*) |
| 161 | b) | O | —C$_{12}$H$_{25}$ | 1.43562 | |
*) = Hexane/Acetic ester = 8:2
| Expl. No. | process | formula | Phys. Const. $n_D^{20}$ or mp (°C.) | $R_F$ |
|---|---|---|---|---|
| 162 | j) | 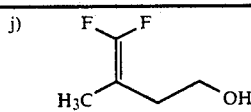 | | 0.26*) |
| 163 | d) | 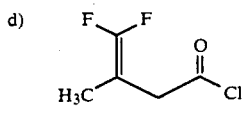 | | |
| 164 | j) | 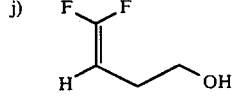 | | 0.21*) |
| 165 | e) | 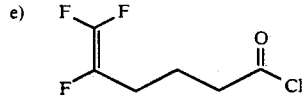 | | |
| 166 | m) | 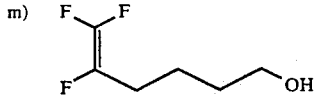 | | |
| 167 | d) | 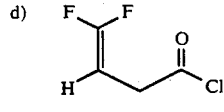 | | |
| 168 | c) | 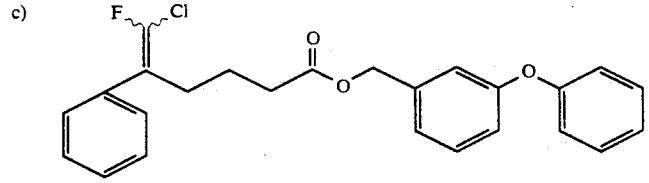 | 1.5902 | |

| | | | |
|---|---|---|---|
| 169 | j) | 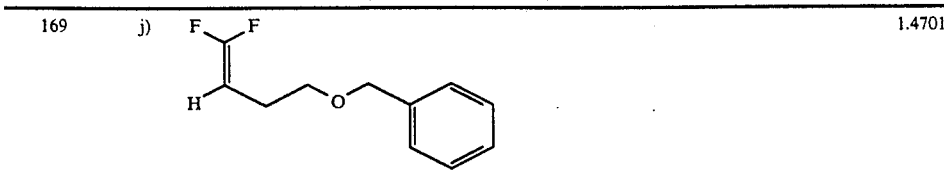 | 1.4701 |
*) = Diethyl ether/Hexane = 1/1
| | | | |
|---|---|---|---|
| 170 | j) | 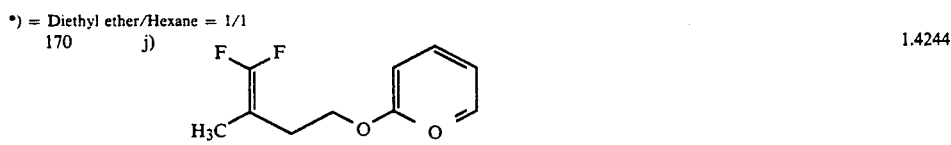 | 1.4244 |
| 171 | i) | 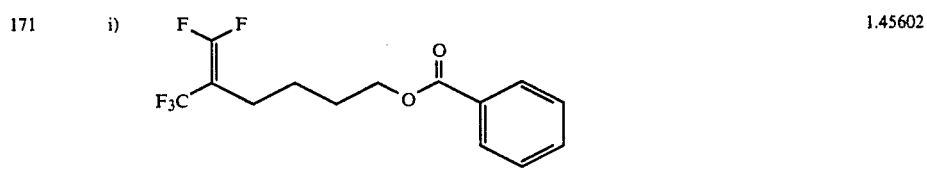 | 1.45602 |
| 172 | i) | 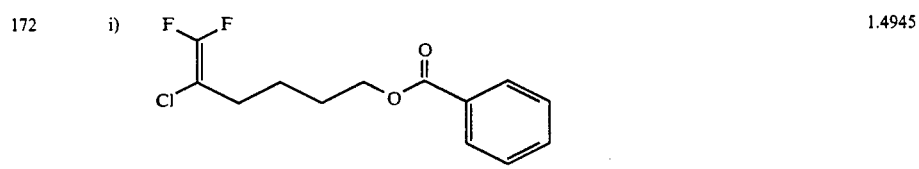 | 1.4945 |
| 173 | h) | 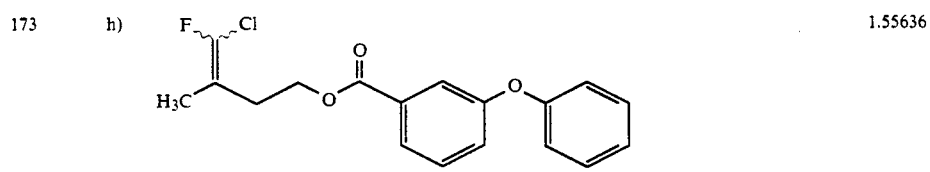 | 1.55636 |
| 174 | h) | 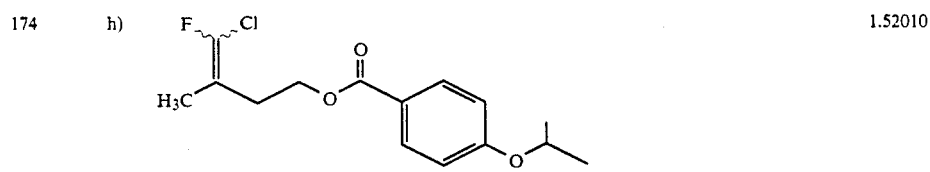 | 1.52010 |
| 175 | m) | 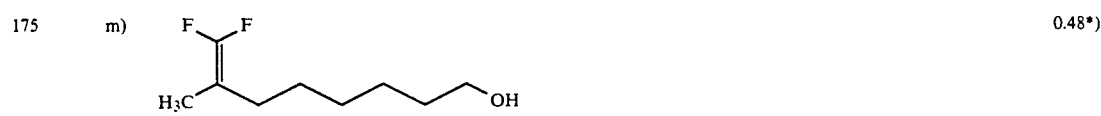 | 0.48*) |
| 176 | i) | 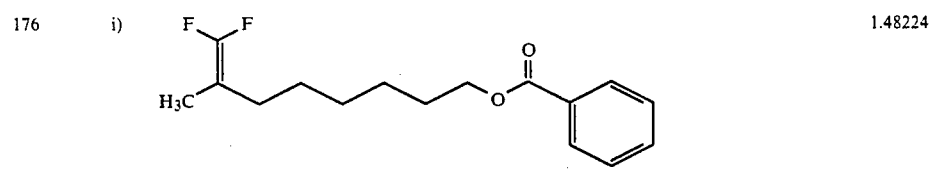 | 1.48224 |
*) Hexane/Acetic ether = 1/1
| | | | |
|---|---|---|---|
| 177 | i) | 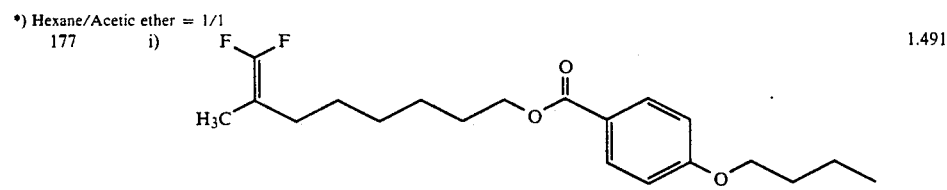 | 1.491 |
| 178 | h) | 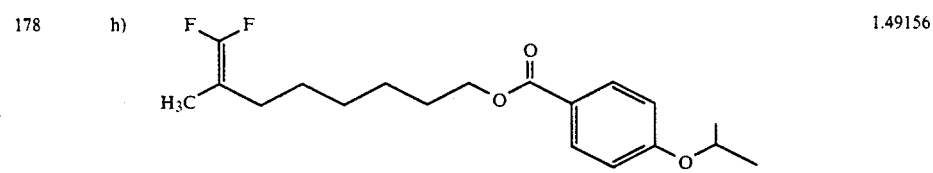 | 1.49156 |

| | | | |
|---|---|---|---|
| 179 | b) | 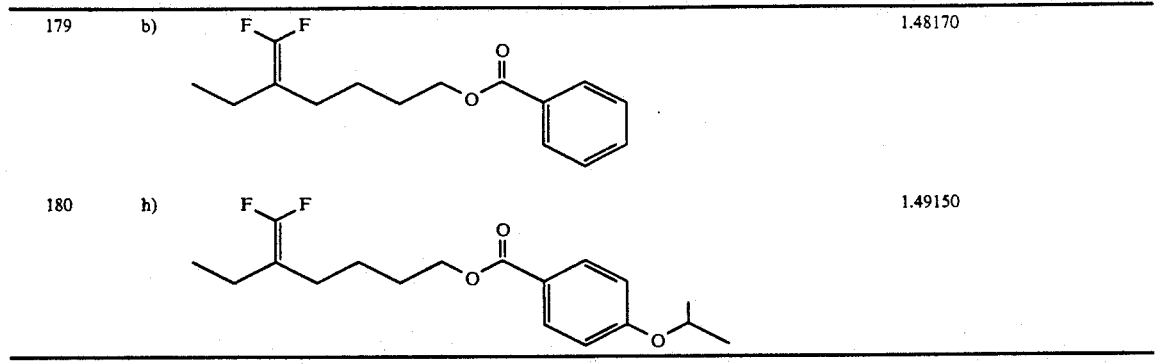 | 1.48170 |
| 180 | h) | | 1.49150 |

The following test Examples demonstrate the biological activity of the compounds of the invention.

Use Example A

Activity in the prophylactic treatment of feed against the against black bean aphids (*Aphis fabae* Scop.)

From the primary leaf of field beans (*Phaseolus vulgaris nanus* Aschers.), 24 mm diameter discs were cut. Some of these were treated with a 0.1% aqueous preparations of compounds of the invention and these along side untreated discs were placed on filter papers with the underside of the leaves turned upwards. After drying the test pieces, they were each infested with wingless stages of *Aphis fabae* (approx 100 per leaf piece). The experiment was replicated 3 times. The leaves were kept on wet filter papers for 2 days at 25° C. and 16 hours light per day. The percentage mortality was then estimated and the activity calculated using Abbott's method in comparison with the untreated controls.

The compounds of Examples 2, 9, 11-15,20, 30, 38, 41, 42, 44, 47-50, 52, 53, 56-60, 62-64, 66-68, 70, 104, 133-139, 168, 169 and 173 showed an activity of 80% or more.

Use Example B

Activity in prophylactic treatment of leaves against brown rice-hoppers (*Nilaparvata lugens* Stal)

Rice seedlings (*Oryzae sativa* L.) in the two leaf stage (about 10 per polystyrene pot of size 6.5×6.5 cm) were either untreated or dipped until dripping wet, with an aqueous preparation containing 0.1% of active material. After drying the sprayed leaves, a transparent cylinder was placed over each pot and through an opening, about 30 brown rice-hoppers (*Nilaparvata lugens*) in the 4-5 stage, anaesthetised with carbon dioxide, were introduced into each pot. After closing the opening with a fine mesh screen, the pots were kept for 2 days at 28° C. and 16 hours/day of light in the glasshouse, the amount of dead hoppers was determined. The percentage mortality was then estimated and the activity calculated using Abbott's method in comparison with the untreated controls.

The compounds of Examples 1, 2, 7, 9, 11, 13-15, 22, 25, 32, 35, 38, 41, 42, 44, 47-50, 52, 53, 56-68, 71, 133-140, 144, 145, 149-153, 155-159, 161, 168, 169 and 176-180 showed an activity cf 80% or more.

Use Example C

Activity in the prophylactic treatment of feed against the two spotted mite (*Tetranychus urticae* Koch)

From the developed primary leaf of field beans (*Phaseolus vulgaris nanus Aschers.*) 14 mm diameter discs were cut. Some of these were treated with a 0.1% aqueous preparations of compounds of the invention and these along side untreated discs were placed on filter papers with the underside of the leaves turned upwards. After drying the test pieces, they were each infested with six adult female *Tetranychus urticae* and maintained for 3 days at 25° C. and 16 hours light per day. The experiment was replicated 4 times. Dead and alive females were then counted and removed. Similarly the number of eggs laid were counted. After a further 7 days, the number of living larvae were counted. The activity was calculated using Abbott's method in comparison with the untreated controls.

The compounds of Examples 1, 2, 3, 5, 7, 9, 11-15, 19-22, 24-26, 28, 30-32, 35, 36, 38, 41, 42, 44, 47-50, 52, 53, 55-68, 70, 71, 74, 101, 104, 105, 108, 128, 133-147, 168, 169 and 171-173 showed 80-100% activity.

Use Example D

Activity in the curative treatment of against eggs of the two spotted mite (*Tetranychus urticae* Koch)

From the developed primary leaf of field beans (*Phaseolus vulgaris nanus Aschers.*) 14 mm diameter discs were cut and layed with the upper surface face down on wet filter paper. Each disc was infested with at least 5 adult female Tetranychus urticae and maintained for 2 days at around 25° C., 50-60% relative humidity and 16 hours light per day. After collecting the adults, the leaf discs with the laid eggs were dipped in a preparation containing 0.0064% of active ingredient and surfactant. As a control, leaf discs were dipped in water containing surfactant in the same concentration as in the preparations containing active ingredient. After counting the eggs, the leaf discs were maintained for 7 days at around 25° C., 50-60% relative humidity and 16 hours light per day. From the percentage difference of laid eggs and living larvae in comparison with the controls, the activity was calculated using Abbott's method. The average of three replicates was recorded.

An activity of 80% or more was shown by the compounds of Examples 2, 7 and 25.

Use Example E

Activity against eggs/larvae of the corn rootworm (*Diabrotica undecimpunctata*)

The compounds of the invention were made up as aqueous emulsions at a concentration of 0.1%. Into the soil in polystyrene petri dishes, containing maize seedlings (1 seedling/dish) and ca. 50 eggs of the corn rootworm (*Diabrotica undecimounctata*) were pipetted 0 2 ml of these preparations. The closed dishes were left at 25° C. under extended daylight conditions for 7 days. The criterion for judging the activity was the death of eggs or newly hatched larvae at the end of the test.

The compounds of Examples 1, 3, 9, 11–15, 21, 26, 31, 41, 42, 44, 47–50, 52, 55–58, 60, 61–68, 105, 128, 133–140, 168, 171 and 176 showed 80–100% activity.

Use Example F

Activity against eggs of the cotton bollworm (*Heliothis viriscens*)

Compounds of the invention were made up as aqueous preparations at a concentration of 0.1%. One day old eggs that had been laid on filter paper by fertilised female moths were dipped in the preparations until they were completely wet and then placed in closed petri dishes under extended daylight conditions for four days at 25° C. The % inhibition of hatching of the eggs in comparison with untreated eggs indicates the level of activity.

The compounds of Examples 9, 11–15, 21, 22, 31, 41, 42, 44, 47–50, 52, 53, 55–68, 70, 128, 133–140, 142, 153, 168, 169 and 171 showed 80–100% activity.

Use Example G

Activity against larvae (L1) of the cotton bollworm (*Heliothis viriscens*)

Compounds of the invention were made up as aqueous preparations at a concentration of 0.1%. Into these, feed material was dipped for 2 seconds. After drying the feed material was put into polystyrene petri dishes. After an hour, 10 L1of the cotton bollworm (*Heliothis viriscens*) were counted into the dishes. The closed dishes were left for up to 7 days at 25° C. under extended daylight conditions. The % mortality of the larvae after two days indicated the level of activity.

The compounds of Examples 11, 13, 15, 41, 42, 44, 49, 50, 52, 56–58, 70, 128, 133, 134 and 136–139 showed 80–100% activity.

Use Example H

Control of root knot nematode (*Meloidogyne incognita*)

An acetone solution and /or a 5% powder preparation of the active ingredient was mixed thoroughly with soil that had been strongly infested with the test nematode. After this the treated soil was put into a 0.5 liter clay pots. Then cucumber seeds were sown or tomato seedlings planted and cultivated at a soil temperature of 25 to 27° C. in a greenhouse. After a cultivation time of 25 to 28 days the cucumber and/or tomato roots were washed and inspected in a water bath for nematode attack (root knots) and the % level of activity of the active ingredients compared with a treated control was determined. When the nematode attack is fully controlled the level of activity is 100%.

At a dose of 10 mg or less of active substance per liter of soil, the compounds of Examples 11, 14, 15, 22, 26, 30, 31, 35, 41, 42, 44, 47–49, 52, 53, 56–58, 60, 62–67, 104, 134–136, 138, 139 and 168 showed 90–100% activity.

Use Example I

Insecticidal activity against sheep blowfly (*Lucilia sericata*)

1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

For the controls the mortality was <5% whereas the compounds of Examples 2, 11, 12–15, 22, 25, 30, 31, 41, 44, 47, 50, 52, 55, 56, 63–65, 68, 74, 101, 105, 138–140, 142, 149, 150 and 152 had an $LC_{50}$ of 300 ppm or less.

Use Example J

Insecticidal activity against house flies (*Musca domestica*)

Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours. The percentage mortality of the insects was then recorded.

Less than 5% mortality resulted in the control treatments whereas the compounds of Examples 13–15, 22, 30, 31, 41, 44, 47, 52, 55, 63–65, 139 and 140 had an $LC_{50}$ of 1000 mg/m² or less.

Use Example K

Activity against ticks (*Boophilus microplus*)

Test compounds were dissolved in a suitable solvent to a desired concentration. Using a microapplicator, 2 microliters of the solution were injected into the blood filled stomach of a tick (*Boophilus microplus*). 5replicate ticks were treated at each concentration and subsequently each tick is retained separately in partitioned petri dish held at 25° C. and >80% R.H., until mortality of ticks or fecundity and viability of eggs produced by survivors could be assessed. The percentage reduction in total reproductive capacity (i.e. the combined effects of adult mortality, reduced fecundity and mortality of eggs) was then recorded and compared with controls. The controls gave less than 5% reduction of reproductive capacity whereas compounds 13, 47, 65 and 138 gave at least 50% reductions of reproductive capacity at a concentration of 500 microgram/tick or less.

We claim:

1. Halogenated olefin of formula I

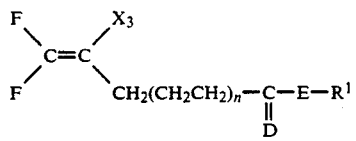

in which
$X_3$ is methyl, ethyl, halomethyl, phenyl or fluorine;
n is 0, 1, 2 or 3 and
in which
D is oxygen,
E is oxygen,
$R^1$ is phenoxybenzyl.

2. An insecticidal and acaricidal composition which comprises a compound as claimed in claim 1 in admixture with an agriculturally acceptable diluent or carrier.

3. A method of combating insects and acarids which comprises applying to the insect or acarid or their locus, an effective amount of a compound claimed in claim 1.

* * * * *